United States Patent
Soeda et al.

(10) Patent No.: US 11,078,518 B2
(45) Date of Patent: Aug. 3, 2021

(54) METHOD FOR EVALUATING BLOOD COAGULATION REACTION

(71) Applicants: CHUGAI SEIYAKU KABUSHIKI KAISHA, Tokyo (JP); PUBLIC UNIVERSITY CORPORATION NARA MEDICAL UNIVERSITY, Nara (JP)

(72) Inventors: Tetsuhiro Soeda, Shizuoka (JP); Takehisa Kitazawa, Shizuoka (JP); Midori Shima, Nara (JP)

(73) Assignees: Chugai Seiyaku Kabushiki Kaisha, Tokyo (JP); Public University Corporation Nara Medical University, Nara (JP)

( * ) Notice: Subject to any disclaimer, the term of this patent is extended or adjusted under 35 U.S.C. 154(b) by 0 days.

(21) Appl. No.: 14/431,425

(22) PCT Filed: Sep. 26, 2013

(86) PCT No.: PCT/JP2013/075978
§ 371 (c)(1),
(2) Date: Mar. 26, 2015

(87) PCT Pub. No.: WO2014/050926
PCT Pub. Date: Apr. 3, 2014

(65) Prior Publication Data
US 2015/0240287 A1    Aug. 27, 2015

(30) Foreign Application Priority Data
Sep. 28, 2012  (JP) .............................. JP2012-217925

(51) Int. Cl.
*C12Q 1/56* (2006.01)
*G01N 33/86* (2006.01)
*C12N 9/64* (2006.01)

(52) U.S. Cl.
CPC ............. *C12Q 1/56* (2013.01); *C12N 9/6443* (2013.01); *G01N 33/86* (2013.01); *G01N 2333/755* (2013.01); *G01N 2333/96452* (2013.01); *G01N 2800/224* (2013.01)

(58) Field of Classification Search
CPC .. C12Q 1/56; C12N 9/6443; G01N 2333/755; G01N 2333/96452; G01N 2800/224; G01N 33/86
See application file for complete search history.

(56) References Cited

U.S. PATENT DOCUMENTS

| | | | |
|---|---|---|---|
| 5,245,014 A | 9/1993 | Kaersgaard | |
| 8,062,635 B2 | 11/2011 | Hattori et al. | |
| 2005/0058640 A1* | 3/2005 | Baxter | C07K 16/40 424/144.1 |
| 2007/0041978 A1* | 2/2007 | Hattori | C07K 16/2866 424/146.1 |
| 2008/0138843 A1 | 6/2008 | Nowak et al. | |
| 2010/0003254 A1 | 1/2010 | Hattori et al. | |
| 2012/0237517 A1 | 9/2012 | Hattori et al. | |

FOREIGN PATENT DOCUMENTS

| | | |
|---|---|---|
| CN | 1044121 C | 7/1999 |
| CN | 1890369 A | 1/2007 |
| CN | 101415445 A | 4/2009 |
| JP | H07506429 A | 7/1995 |
| JP | 2746386 B2 | 5/1998 |
| JP | 2007-504812 A | 3/2007 |
| JP | 2008-530992 A | 8/2008 |
| WO | WO 93/22453 A1 | 11/1993 |
| WO | WO 98/44352 A1 | 10/1998 |
| WO | WO 2005/025615 A2 | 3/2005 |
| WO | WO 2005/035756 A1 | 4/2005 |
| WO | WO 2006/109592 A1 | 10/2006 |
| WO | WO 2007/126808 A1 | 11/2007 |
| WO | WO 2012/067176 A1 | 5/2012 |
| WO | WO 2013/028069 A1 | 2/2013 |

OTHER PUBLICATIONS

Dargaud et al. "Evaluation of thrombin generating capacity in plasma from patients with haemophilia A and B" Thromb Haemost 2005; 93: 475-80 (Year: 2005).*
Astermark, J., "When to start and when to stop primary prophylaxis in patients with severe haemophilia," *Haemophilia* 9:32-37, Blackwell Publishing Ltd., United States (2003).
Hemker, H.C., et al., "Calibrated Automated Thrombin Generation Measurement in Clotting Plasma," *Pathophysiol. Haemost. Thromb.* 33:4-15, S. Karger AG, Switzerland (2003).
Kitazawa, T., et al., "A bispecific antibody to factors IXa and X restores factor VIII hemostatic activity in a hemophilia A model," *Nature Medicine* 18(10):1570-1574, Nature Publishing Group, United Kingdom (2012).
Matsumoto, T., et al., "A modified thrombin generation test for investigating very low levels of factor VIII activity in hemophilia A," *Int. J. Hematol.* 90:576-582, Springer, Japan (2009).
McIntosh, J.H., et al., "A modified thrombin generation test for the measurement of factor VIII concentrates," *Journal of Thrombosis and Haemostasis* 1:1005-1011, International Society on Thrombosis and Haemostasis, United States (2003).

(Continued)

*Primary Examiner* — Blaine Lankford
(74) *Attorney, Agent, or Firm* — Nixon & Vanderhye, P.C.

(57) ABSTRACT

Various methods for evaluating hemostatic effect and various blood coagulation initiation reagents were studied to construct a method for evaluating blood coagulation reaction mediated by a substance having an activity of substituting for coagulation factor VIII (FVIII). As a result, it was discovered that by using a coagulation initiation reagent containing activated coagulation factor XI (FXIa) and phospholipids, the effect of a substance having an activity of substituting for coagulation factor VIII (FVIII) on blood coagulation reaction can be evaluated using the amount of thrombin generated in the blood sample as an indicator.

8 Claims, 2 Drawing Sheets
Specification includes a Sequence Listing.

(56) References Cited

OTHER PUBLICATIONS

Ninivaggi, M., et al., "Thrombin generation assay using factor IXa as a trigger to quantify accurately factor VIII levels in haemophilia A," *Journal of Thrombosis and Haemostasis* 9:1549-1555, International Society on Thrombosis and Haemostasis, United States (2011).

Sampei, Z., et al., "Identification and Multidimensional Optimization of an Asymmetric Bispecific IgG Antibody Mimicking the Function of Factor VIII Cofactor Activity," *PLOS ONE* 8(2):1-13, Public Library of Science, United States (2013).

International Search Report for International Patent Application No. PCT/JP2013/075978, Japanese Patent Office, Japan, dated Dec. 17, 2013.

Unverified English language translation of WO 2005/035756 A1, published Apr. 21, 2005, in the name of Chugai Seiyaku Kabushiki Kaisha.

Unverified English language translation of WO 2006/109592 A1, published Oct. 19, 2006, in the name of Chugai Seiyaku Kabushiki Kaisha.

Unverified English language translation of WO 2012/067176 A1, published on May 24, 2012, in the name of Chugai Seiyaku Kabushiki Kaisha.

Kitchen, S., et al., "Lipid composition of seven APTT reagents in relation to heparin sensitivity," *British Journal of Haematology* 106:801-808, Blackwell Science Ltd., England (1999).

Poller, L., "Activated partial thromboplastin time (APTT)," in *Laboratory Techniques in Thrombosis—a Manual* 37-44 (J. Jespersen et al. ed., Kluwer Academic Publishers 1999).

\* cited by examiner (A)

(B)

METHOD FOR EVALUATING BLOOD COAGULATION REACTION

REFERENCE TO SEQUENCE LISTING SUBMITTED ELECTRONICALLY

The content of the electronically submitted sequence listing (Name: 21440730001sequence.txt; Size: 10 KB; and Date of Creation: Mar. 26, 2015) filed with the application is incorporated herein by reference in its entirety.

TECHNICAL FIELD

The present invention relates to methods for evaluating blood coagulation reaction mediated by a substance having an activity of functionally substituting for coagulation factor VIII (FVIII). Furthermore, the present invention relates to reagents for evaluating blood coagulation reaction which contain activated coagulation factor XI (FXIa); and kits containing such a reagent, for evaluating blood coagulation reaction mediated by a substance having an activity of functionally substituting for coagulation factor VIII.

BACKGROUND ART

Hemophilia is a hemorrhagic disease caused by congenital deficiency or dysfunction of coagulation factor VIII (FVIII) or coagulation factor IX (FIX). The former is referred to as hemophilia A and the latter as hemophilia B. Their genes are both located on the X chromosome, and their genetic abnormalities are transmitted by sex-linked recessive inheritance. Thus, more than 99% of the patients who develop the disease are men. It is known that the prevalence rate is approximately one in 10,000 live male births, and the ratio between hemophilia A and hemophilia B is approximately 5:1.

In hemophilia patients, major bleeding sites are, for example, intraarticular, intramuscular, subcutaneous, intraoral, intracranial, digestive tracts, and intranasal. In particular, repeated intraarticular bleeding could develop articular disorders or hemophilic arthropathy accompanying difficulty in walking, and in some cases eventually require joint replacement surgery. This is therefore a major factor that decreases the quality of life (QOL) of hemophilia patients.

The severity of hemophilia correlates well with the activity of FVIII or FIX in blood. Patients with activity of less than 1% are classified as severe, patients with activity of 1% or more and less than 5% are classified as moderate, and patients with activity of 5% or more and less than 40% are classified as mild. Severe patients, who account for approximately half of the hemophilia patients, exhibit bleeding symptoms several times a month, which is markedly frequent as compared to moderate and mild patients. Therefore, in severe hemophilia patients, maintaining the activity of FVIII or FIX in the blood at 1% or more by FVIII or FIX replacement therapy may be effective for preventing manifestation of bleeding symptoms (Non-Patent Document 1).

In addition to hemophilia and acquired hemophilia, von Willebrand's disease, which is caused by dysfunction or deficiency of von Willebrand factor (vWF), is known as a related bleeding abnormality. vWF is necessary for platelets not only to properly adhere to subendothelial tissues at a damaged site in the blood vessel wall, but also to form a complex with FVIII and keep the normal blood level of FVIII. These functions are decreased in von Willebrand's disease patients, causing hemostasis dysfunction.

To prevent and/or treat bleeding in hemophilia patients, blood coagulation factors purified from plasma or produced by genetic recombination techniques are mainly used.

Known methods for monitoring the efficacy of blood coagulation factors such as FVIII include activated partial thromboplastin time (APTT), APTT-based one-stage coagulation method, and thrombin generation assay (TGA). APTT and one-stage coagulation method have long been widely used as methods for monitoring the efficacy of FVIII formulations. APTT is a method of measuring the time required for conversion of fibrinogen to insoluble fibrin after adding an APTT reagent and then $CaCl_2$ to a test plasma, that is, the time until the initiation of coagulation. The one-stage coagulation method is a method of measuring coagulation time by the same method as APTT in a FVIII-deficient plasma to which a test plasma diluted with a buffer at a certain ratio has been added, and determining the activity of FVIII in the test plasma based on a calibration curve that has been obtained by using serial dilutions of normal plasma instead of the test plasma. TGA is an assay for measuring the amount of thrombin generated over time as the coagulation reaction progresses, where the amount of thrombin is measured as enzymatic activity using a fluorogenic substrate for thrombin (Non-Patent Document 2). TGA enables evaluation of a series of coagulation reactions, from the initiation of thrombin generation in the coagulation reaction up to thrombin generation in the amplification phase of the coagulation reaction. Furthermore, for coagulation initiation reagents for TGA, there are reports of reagents in which a low-concentration phospholipid solution (4 µM) is used as a base and combined with a low-concentration tissue factor (Non-Patent Document 2), combined with FIXa (Non-Patent Documents 3 and 4), combined with FXII-activating agent (ellagic acid) (Non-Patent Document 5), or combined with a mixed solution of low-concentration tissue factor and an FXII-activating agent (ellagic acid) (Non-Patent Document 5).

Recently, bispecific antibodies that bind to both activated coagulation factor IX (FIXa) and coagulation factor X (FX), and substitute for the cofactor function of FVIII, i.e. the function of promoting the activation of FX by FIXa, were found (Patent Documents 1 to 3). However, while such bispecific antibodies functionally substitute for FVIII, the mechanism of manifestation of their actions is not completely the same as that of FVIII. For example, FVIII shows the cofactor activity only when activated by FXa or thrombin; however, the above-mentioned bispecific antibodies do not need such an activation process to show the cofactor activity. Therefore, it was not necessarily possible to apply the existing methods for monitoring the efficacy of FVIII to such antibodies.

PRIOR ART DOCUMENTS

Non-Patent Documents

[Non-Patent Document 1] Astermark J. Haemophilia. 2003 9(Suppl.1) 32

[Non-Patent Document 2] Pathophysiol Haemost Thromb. 2003; 33(1):4

[Non-Patent Document 3] J Thromb Haemost. 2011 August; 9(8):1549-55.

[Non-Patent Document 4] J Thromb Haemost. 2003 May; 1(5):1005-11.

[Non-Patent Document 5] Int J Hematol. 2009 December; 90(5):576-82.

Patent Documents

[Patent Document 1] WO2005/035756
[Patent Document 2] WO2006/109592
[Patent Document 3] WO2012/067176

SUMMARY OF THE INVENTION

Problems to be Solved by the Invention

The present invention was achieved in view of the above circumstances. An objective of the present invention is to provide methods for evaluating the efficacy of a substance in a blood coagulation reaction wherein the substance has an activity of substituting for coagulation factor VIII (FVIII); blood coagulation initiation reagents to be used in such methods; and kits containing such a reagent.

Means for Solving the Problems

To solve the above-mentioned problems, the present inventors studied various methods for evaluating hemostatic effect and various blood coagulation initiation reagents to construct a method for evaluating blood coagulation reaction mediated by a substance having an activity of substituting for coagulation factor VIII (FVIII). As a result, the present inventors found that, by using a blood coagulation initiation reagent containing activated coagulation factor XI (FXIa), the effect of a substance having an activity of substituting for coagulation factor VIII (FVIII) on blood coagulation reaction can be evaluated with appropriate sensitivity using the amount of thrombin generated in a blood sample as an indicator. Furthermore, the present inventors successfully discovered a method for thrombin generation assay using a blood coagulation initiation reagent containing activated coagulation factor XI (FXIa). The present invention is based on these findings, and relates to the following:

[1] a method for evaluating blood coagulation reaction mediated by a substance having an activity of substituting for coagulation factor VIII, wherein the method comprises the steps of:
(i) adding a blood coagulation initiation reagent comprising activated coagulation factor XI to a blood-derived sample isolated from a subject, wherein the sample comprises the substance having an activity of substituting for coagulation factor VIII; and
(ii) measuring the amount of thrombin generated in the blood-derived sample obtained in step (i);
[2] the method of claim 1, wherein the substance having an activity of substituting for coagulation factor VIII is a bispecific antibody that binds to coagulation factor IX or activated coagulation factor IX, and to coagulation factor X;
[3] the method of claim 1 or 2, wherein the subject is a hemorrhagic disease patient;
[4] the method of claim 3, wherein the hemorrhagic disease is a disease caused by decreased or deficient activity of coagulation factor VIII or activated coagulation factor VIII;
[5] the method of claim 3 or 4, wherein the hemorrhagic disease is a disease selected from the group consisting of hemophilia, acquired hemophilia, and von Willebrand's disease caused by dysfunction or deficiency of von Willebrand factor (vWF);
[6] the method of any one of claims 1 to 5, wherein the blood coagulation initiation reagent is a reagent comprising activated coagulation factor XI and a phospholipid;
[7] a blood coagulation initiation reagent for use in the method of any one of claims 1 to 6, which comprises activated coagulation factor XI;
[8] the blood coagulation initiation reagent of claim 7, which further comprises a phospholipid; and
[9] a kit for use in the method of any one of claims 1 to 6, which comprises the blood coagulation initiation reagent of claim 7 or 8.

Effects of the Invention

The present invention provides methods for evaluating blood coagulation reaction mediated by a substance having an activity of substituting for coagulation factor VIII, in which the amount of thrombin generated in a blood-derived sample is used as an indicator. Substances having an activity of substituting for coagulation factor VIII, in particular, bispecific antibodies that bind to coagulation factor IX or activated coagulation factor IX and to coagulation factor X, express the cofactor activity by a mechanism that is not completely the same as that of coagulation factor VIII. Therefore, in treating hemorrhagic diseases such as hemophilia with a bispecific antibody, it is not necessarily possible to apply widely-used efficacy evaluation methods, and therefore appropriate evaluation of the effect of the bispecific antibody may not be possible. The present invention enables accurate evaluation of even the above-mentioned bispecific antibodies for their effect in treating hemorrhagic diseases.

MODE FOR CARRYING OUT THE INVENTIONS

Figure 1:
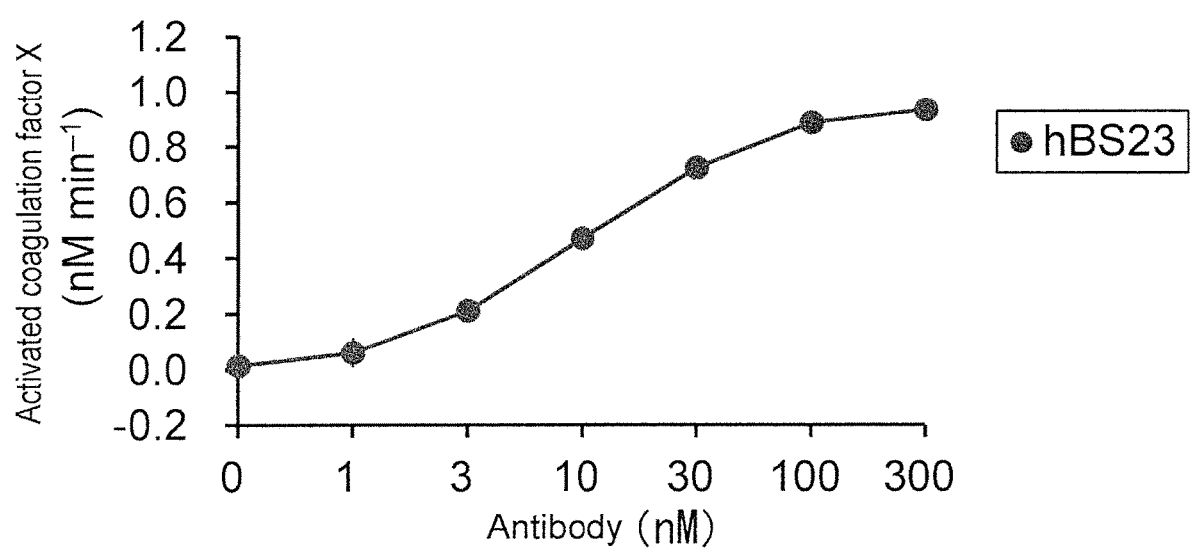
FIG. 1 shows the FVIII function-substituting activity of hBS23, which is one of the bispecific antibodies that bind to activated coagulation factor IX and coagulation factor X. hBS23 showed activity of enhancing FXa generation in the presence of FIXa/FX/phospholipids.

The present invention relates to methods for evaluating blood coagulation reaction by a substance having an activity of substituting for coagulation factor VIII, wherein the method comprises the steps of:
(i) adding a blood coagulation initiation reagent comprising activated coagulation factor XI to a blood-derived sample isolated from a subject, wherein the sample comprises the substance having an activity of substituting for coagulation factor VIII; and (ii) measuring the amount of thrombin generated in the blood-derived sample obtained in step (i).

By using the methods of the present invention, the cofactor activity of a substance having an activity of substituting for coagulation factor VIII can be evaluated appropriately. In particular, as compared to activated partial thromboplastin time (APTT)-based methods or thrombin generation assay based on induction by a coagulation initiation reagent containing a low concentration of tissue factor, which have been conventionally widely used as methods for monitoring the efficacy of a blood coagulation factor, the methods of the present invention allow monitoring of hemostatic effect with more appropriate sensitivity.

In the present invention, "a method for evaluating blood coagulation reaction mediated by a substance having an activity of substituting for coagulation factor VIII" can be rephrased as "a method for evaluating the cofactor activity of a substance having an activity of substituting for coagulation factor VIII". It may also be rephrased as "a method for evaluating the therapeutic effect of a substance having an activity of substituting for coagulation factor VIII on hemorrhagic diseases". Alternatively, it may be rephrased as "a method for evaluating the prophylactic effect of a substance having an activity of substituting for coagulation factor VIII on hemorrhagic diseases". Furthermore, the "method for evaluating" can also be expressed as "method for determining" or "method for measuring".

Coagulation factor VIII is one of a series of molecules involved in blood coagulation. It exhibits cofactor activity when it is activated by thrombin or activated coagulation factor X, and promotes the activation reaction of coagulation factor X by activated coagulation factor IX. Substances having an activity of substituting for coagulation factor VIII of the present invention are similar to coagulation factor VIII in that they promote the activation of coagulation factor X by activated coagulation factor IX; however, they are different from coagulation factor VIII in that, for example, they do not require activation by thrombin or activated coagulation factor X.

A "substance having an activity of substituting for coagulation factor VIII" of the present invention can be rephrased as a "substance having coagulation factor VIII-like activity". In the present invention, the phrase "functionally substitute for coagulation factor VIII" means that a substance recognizes coagulation factor IX (FIX) or coagulation factor IXa (FIXa), and coagulation factor X (FX), and promotes activation of FX by FIXa (promotes generation of FXa by FIXa). FXa generation-promoting activity can be evaluated using, for example, a measurement system composed of FIXa, FX, synthetic substrate S-2222 (synthetic substrate of FXa), and phospholipids. Such a measurement system shows a correlation with disease severity and clinical symptoms in hemophilia A cases (Rosen S, Andersson M, Blomback M et al. Clinical applications of a chromogenic substrate method for determination of FVIII activity. Thromb Haemost 1985; 54: 811-23).

Preferred embodiments of the substance having an activity of functionally substituting for coagulation factor VIII in the present invention include, for example, bispecific antibodies which bind to coagulation factor IX or activated coagulation factor IX and to coagulation factor X. Such antibodies can be obtained according to methods described in, for example, WO2005/035756, WO2006/109592, and WO2012/067176. Specifically, antibodies can be prepared using genetic recombination techniques known to those skilled in the art based on the sequences of an antibody against coagulation factor IX and/or activated coagulation factor IX and an antibody against coagulation factor X. A polynucleotide encoding an antibody can be constructed based on the sequences of an antibody against coagulation factor IX and/or activated coagulation factor IX and an antibody against coagulation factor X, and then inserted into an expression vector, and subsequently expressed in an appropriate host cell (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

Bispecific antibodies of the present invention can be isolated from inside host cells or from outside the cells (medium, or such), and purified to substantial purity and homogeneity. Separation and purification of antibodies can be performed by methods routinely used for separating and purifying antibodies, and are not limited to particular methods. For example, antibodies can be separated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectrofocusing, dialysis, recrystallization, and such. Bispecific antibodies of the present invention include antibodies described in, for example, WO2005/035756, WO2006/109592, and WO2012/067176.

A bispecific antibody contains a first antigen-binding site and a second antigen-binding site that can specifically bind to at least two different antigens. The first antigen-binding site and the second antigen-binding site are not particularly limited as long as they have an activity of binding to coagulation factor IX and/or activated coagulation factor IX and to coagulation factor X, respectively, but include, for example, sites necessary for antigen binding that are present in antibodies, scaffold molecules (antibody-like molecules), peptides, and such, or fragments containing such sites. Scaffold molecules are molecules that exhibit function by binding to target molecules. Any polypeptides may be used as long as they are conformationally stable polypeptides that can bind to at least one target antigen. Examples of such polypeptides include antibody variable regions, fibronectin (WO 2002/032925), protein A domain (WO 1995/001937), LDL receptor A domain (WO 2004/044011, WO 2005/040229), ankyrin (WO 2002/020565), and such, and also molecules described in Nygren et al. (Current Opinion in Structural Biology, 7: 463-469 (1997); and Journal of Immunol Methods, 290: 3-28 (2004)), Binz et al. (Nature Biotech 23: 1257-1266 (2005)), and Hosse et al. (Protein Science 15: 14-27 (2006)). Furthermore, as mentioned in Curr Opin Mol Ther. 2010 August; 12(4): 487-95 and Drugs. 2008; 68(7): 901-12, peptide molecules that can bind to target antigens may also be used.

Bispecific antibodies can be produced by, for example, using genetic recombination techniques (see, for example, Borrebaeck C A K and Larrick J W, THERAPEUTIC MONOCLONAL ANTIBODIES, Published in the United Kingdom by MACMILLAN PUBLISHERS LTD, 1990). Recombinant antibodies can be obtained by cloning DNAs encoding them from hybridomas or antibody-producing cells such as sensitized lymphocytes that produce antibodies, inserting them into suitable vectors, and then introducing them into hosts (host cells) to produce the antibodies.

Bispecific antibodies may include not only whole antibodies but also antibody fragments and low-molecular-weight antibodies (minibodies), and modified antibodies.

For example, antibody fragments or minibodies include diabodies (Dbs), linear antibodies, and single chain antibody (hereinafter, also denoted as scFvs) molecules. Herein, an "Fv" fragment is the smallest antibody fragment that contains a complete antigen recognition site and binding site.

Bispecific antibodies include human antibodies, mouse antibodies, rat antibodies, and such, and their origins are not limited. They may also be genetically modified antibodies, such as chimeric or humanized antibodies.

Methods for obtaining human antibodies are known in the art. For example, transgenic animals carrying the entire repertoire of human antibody genes can be immunized with desired antigens to obtain desired human antibodies (see International Patent Application WO 93/12227, WO 92/03918, WO 94/02602, WO 94/25585, WO 96/34096, and WO 96/33735).

Genetically modified antibodies can also be produced using known methods. Specifically, for example, chimeric antibodies are composed of H chain and L chain variable regions of an immunized animal antibody, and H chain and L chain constant regions of a human antibody. Chimeric antibodies can be obtained by linking DNAs encoding the variable regions of the antibody derived from the immunized animal, with DNAs encoding the constant regions of a human antibody, inserting this into an expression vector, and then introducing it into host cells to produce the antibodies.

Humanized antibodies are modified antibodies also referred to as reshaped human antibodies. A humanized antibody is constructed by transferring the CDRs of an antibody derived from an immunized animal to the complementarity determining regions of a human antibody. Conventional genetic recombination techniques for such purposes are known (see European Patent Application Publication No. EP 239400; International Publication No. WO 96/02576; Sato K et al., Cancer Research 1993, 53: 851-856; International Publication No. WO 99/51743).

In the present invention, a blood-derived sample containing a substance having an activity of substituting for coagulation factor VIII is isolated from a subject. Such a blood sample can be obtained from a subject to whom a substance having an activity of substituting for coagulation factor VIII has been administered. Subjects include patients with hemorrhagic symptoms at any part of the body (hemorrhagic disease patients). Major bleeding sites include, for example, intraarticular, intramuscular, subcutaneous, intraoral, intracranial, digestive tract, and intranasal sites, but are not limited thereto. Hemorrhagic disease patients preferably include patients with a hemorrhagic disease caused by decreased or deficient activity of coagulation factor VIII and/or activated coagulation factor VIII. Examples of patients with a hemorrhagic disease caused by decreased or deficient activity of coagulation factor VIII and/or activated coagulation factor VIII include patients with a hemorrhagic symptom who have congenital or acquired, decreased or deficient activity of either or both of coagulation factor VIII and activated coagulation factor VIII. Decreased activity of coagulation factor VIII and activated coagulation factor VIII refers to, for example, a patient in which the activity of these factors is preferably less than 40% (for example, less than 40%, less than 30%, less than 20%, or less than 10%), more preferably less than 10% (for example, less than 10%, less than 9%, less than 8%, less than 7%, and less than 6%), even more preferably less than 5% (for example, less than 5%, less than 4%, less than 3%, or less than 2%), and particularly preferably less than 1% than that of a healthy individual, but is not limited thereto. Methods for determining the activity of coagulation factor VIII and activated coagulation factor VIII are well-known to those skilled in the art (for example, "Minna ni yakudatsu ketsuyuubyou no kiso to rinshou (Widely useful basics and clinics of hemophilia)" Shirahata, A., Iyaku (Medicine and Drug) Journal, 2009).

More specifically, an example of such diseases is selected from hemophilia (hemophilia A and hemophilia B), acquired hemophilia, and von Willebrand's disease caused by dysfunction or deficiency of von Willebrand factor (vWF), but is not limited thereto. Blood-derived samples include serum, plasma, or whole blood. In the present invention, plasma samples are preferably used. Methods for obtaining blood-derived samples from subjects are well-known to those skilled in the art.

In the present invention, activated coagulation factor XI, or a blood coagulation initiation reagent containing activated coagulation factor XI, is added to blood-derived samples obtained from the above-mentioned subjects.

The activated coagulation factor XI of the present invention can be purified and prepared by activating coagulation factor XI using activated coagulation factor XII, thrombin, or such, and purifying it by chromatography such as ion exchange, reverse phase, or gel filtration chromatography, or by affinity chromatography with a column onto which an anti-activated coagulation factor XI antibody is immobilized, or by further combining a plurality of these columns.

The amino acid sequence of human coagulation factor XI and the nucleotide sequence of the nucleic acid encoding this amino acid sequence are known as GenBank: NP_000119 (SEQ ID NO: 2) and NM_000128 (SEQ ID NO: 1), respectively. However, coagulation factor XI mentioned herein is not limited to human coagulation factor XI, and it may be of other animal species (for example, horse, bovine, pig, rabbit, rat, or mouse). Coagulation factor XI can be a naturally occurring protein, or can be prepared as a recombinant protein using known genetic recombination techniques. Recombinant proteins can be prepared by methods known to those skilled in the art. A recombinant protein can be prepared, for example, by inserting a nucleic acid encoding coagulation factor XI to a suitable expression vector, introducing this into a suitable host cell and collecting a resultant transformant, obtaining an extract, and then purifying it by chromatography such as ion exchange, reverse phase, or gel filtration chromatography, or by affinity chromatography with a column onto which an anti-coagulation factor XI antibody is immobilized, or by further combining a plurality of these columns.

Furthermore, when coagulation factor XI is expressed in a host cell (for example, animal cells or *Escherichia coli*) as a fusion polypeptide with glutathione S-transferase protein, or as a recombinant polypeptide with several additional histidines, the expressed recombinant polypeptide can be purified using a glutathione column or a nickel column.

When *E. coli* is used as a host for example, the above mentioned vector is not particularly limited as long as it has "ori" for amplification in *E. coli* so that the vector is amplified and prepared in a large scale in *E. coli* (such as JM109, DH5α, HB101, XL1Blue), and further has a gene for selection of transformed *E. coli* (for example, a drug resistance gene that allows screening with a certain drug (ampicillin, tetracycline, kanamycin, chloramphenicol). Examples of such vectors include M13 vectors, pUC vectors, pBR322, pBluescript, pCR-Script, and such. Alternatively, when aiming to subclone and excise cDNA, the vectors include, for example, pGEM-T, pDIRECT, pT7, and such, in addition to the vectors described above. Expression vectors are particularly useful when using vectors for producing coagulation factor XI. For example, when aiming for expression in E. coli such as JM109, DH5a, HB101, and XL1-Blue, the expression vectors not only have the characteristics that allow vector amplification in E. coli, but must also carry a promoter that allows efficient expression in E. coli, for example, lacZ promoter (Ward et al., Nature (1989) 341: 544-546; FASEB J. (1992) 6: 2422-2427), araB promoter (Better et al., Science (1988) 240: 1041-1043), T7 promoter or such. Such vectors include pGEX-5X-1 (Pharmacia), "QIAexpress system" (Qiagen), pEGFP, pET, and such, in addition to the vectors described above.

The vectors may also contain a signal sequence for polypeptide secretion. As a signal sequence for polypeptide secretion, a pelB signal sequence (Lei, S. P. et al J. Bacteriol. (1987) 169: 4379) may be used when a polypeptide is secreted into the E. coli periplasm. Introduction of a vector into host cells can be performed by calcium chloride or electroporation methods, for example.

In addition to vectors for E. coli, the vectors include mammalian expression vectors (for example, pcDNA3 (Invitrogen), pEGF-BOS (Nucleic Acids. Res. 1990, 18(17): p 5322), pEF, and pCDM8), insect cell-derived expression vectors (for example, the "BAC-TO-BAC® baculovirus expression system" (Gibco-BRL) and pBacPAK8), plant-derived expression vectors (for example, pMH1 and pMH2), animal virus-derived expression vectors (for example, pHSV, pMV, and pAdexLcw), retroviral expression vectors (for example, pZIPneo), yeast expression vectors (for example, "Pichia Expression Kit" (Invitrogen), pNV11, and SP-Q01), and Bacillus subtilis expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277: 108), MMLV-LTR promoter, EF 1a promoter (Mizushima et al., Nucleic Acids Res. (1990) 18: 5322), CMV promoter, and such, and more preferably they have a gene for selecting transformed cells (for example, a drug resistance gene that allows screening using a drug (neomycin, G418, or such)). Vectors with such characteristics include pMAM, pDR2, pBK-RSV, pBK-CMV, pOPRSV, and pOP13, for example.

Systems for producing a polypeptide in vivo include, for example, production systems using an animal or plant. A nucleic acid encoding coagulation factor XI is introduced into an animal or plant, and coagulation factor XI is produced in the body of the animal or plant and then collected.

When an animal is used, production systems using a mammal or insect can be used. Mammals that can be used include goats, pigs, sheep, mice, and cattle (Vicki Glaser, SPECTRUM Biotechnology Applications, 1993). When a mammal is used, a transgenic animal can be used.

Coagulation factor XI obtained as described above can be isolated from inside host cells or from outside the cells (the medium, or such), and purified as a substantially pure and homogeneous polypeptide. Isolation and purification of a peptide can be performed by methods routinely used for isolating and purifying polypeptides, and is not particularly limited. For example, polypeptides can be isolated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectrofocusing, dialysis, recrystallization, and such.

Optional modification or partial peptide removal is also possible by allowing an appropriate protein modification enzyme to act on coagulation factor XI before or after purification. Examples of protein modification enzymes that may be used include trypsin, chymotrypsin, lysyl endopeptidase, protein kinase, and glucosidase.

Furthermore, coagulation factor XI also includes proteins that have one or more amino acid alterations and are potentially capable of activating coagulation factor IX into activated coagulation factor IX. To this extent, fragments of coagulation factor XI are also included.

When an amino acid residue is altered, the amino acid is preferably mutated for a different amino acid(s) that conserves the properties of the amino acid side-chain. Examples of amino acid side chain properties are: hydrophobic amino acids (A, I, L, M, F, P, W, Y, and V), hydrophilic amino acids (R, D, N, C, E, Q, H, K, S, and T), amino acids containing aliphatic side chains (G, A, V, L, I, and P), amino acids containing hydroxyl group-containing side chains (S, T, and Y), amino acids containing sulfur-containing side chains (C and M), amino acids containing carboxylic acid- and amide-containing side chains (D, N, E, and Q), amino acids containing basic side chains (R, K, and H), and amino acids containing aromatic side chains (H, F, Y, and W) (amino acids are represented by one-letter codes in parentheses). Amino acid substitutions within each group are called conservative substitutions. It is already known that a polypeptide containing a modified amino acid sequence in which one or more amino acid residues (e.g. 2, 3, 4, 5, 10, 20, 30, 40, 50, or 100 residues) in a given amino acid sequence are deleted, added, and/or substituted with other amino acids can retain the original biological activity (Mark, D. F. et al., Proc. Natl. Acad. Sci. USA; (1984) 81: 5662-6; Zoller, M. J. and Smith, M., Nucleic Acids Res. (1982) 10: 6487-500; Wang, A. et al., Science (1984) 224: 1431-3; Dalbadie-McFarland, G et al., Proc. Natl. Acad. Sci. USA (1982) 79: 6409-13). Such mutants have an amino acid identity of at least 70%, more preferably at least 75%, even more preferably at least 80%, still more preferably at least 85%, yet more preferably at least 90%, and most preferably at least 95%, with the coagulation factor XI or coagulation factor XI fragment before the amino acid alteration. Herein, sequence identity is defined as the percentage of residues identical to those in the original amino acid sequence of the heavy chain variable region or light chain variable region, determined after the sequences are aligned and gaps are appropriately introduced to maximize the sequence identity as necessary.

The identity of nucleotide sequences or amino acid sequences can be determined using the algorithm BLAST by Karlin and Altschul (Proc. Natl. Acad. Sci. USA 87:2264-2268, 1990; and Proc. Natl. Acad. Sci. USA 90: 5873, 1993). Programs called BLASTN and BLASTX have been developed based on the BLAST algorithm (Altschul S F et al., J. Mol. Biol. 215: 403, 1990). When nucleotide sequences are analyzed using BLASTN, the parameters are, for example, score=100 and wordlength=12. When amino acid sequences are analyzed using BLASTX, the parameters are, for example, score=50 and wordlength=3. When the BLAST and gapped BLAST programs are used, the default parameters for each program are used. Specific techniques for these analysis methods are known in the art.

Methods for preparing a DNA encoding a protein with a modified amino acid sequence that are known to those skilled in the art include site-directed mutagenesis (Kramer, W. and Fritz, H.-J. (1987) Oligonucleotide-directed construction of mutagenesis via gapped duplex DNA. Methods in Enzymology, 154: 350-367), hybridization techniques (Southern, E. M. (1975) Journal of Molecular Biology, 98, 503), and PCR techniques (Saiki, R. K. et al. (1985) Science, 230, 1350-1354; Saiki, R. K. et al. (1988) Science, 239, 487-491).

In the present invention, it is preferred to add phospholipids to activated coagulation factor XI. The phospholipids are not particularly limited in the present invention. Examples of the phospholipids include phosphatidylserine, phosphatidylcholine, phosphatidylethanolamine, phosphatidylinositol, phosphatidylglycerol, diphosphatidylglycerol, and sphyngomyelin, and combination of two or more of them, but are not limited thereto. In the present invention, the combination of phosphatidylserine, phosphatidylcholine, and phosphatidylethanolamine is preferred.

In the present invention, activated coagulation factor XI can be used in the form of a reagent and added to blood-derived samples isolated from subjects. In the present invention, such a reagent is referred to as a "blood coagulation initiation reagent". The "blood coagulation initiation reagent" of the present invention may contain phospholipids and salts of calcium, magnesium, and such, in addition to activated coagulation factor XI.

Activated coagulation factor XI and/or phospholipids can be added to a blood-derived sample at an amount sufficient for measuring the amount of thrombin generation which will be described later. Activated coagulation factor XI can be added, for example, at an amount from 0.00001 pmol to 1000 nmol per mL of plasma sample, without being limited thereto. Furthermore, phospholipids can be added, for example, at an amount between 0.001 nmol to 10000 nmol per mL of plasma sample, without being limited thereto.

In the present invention, the amount of thrombin generated in a blood-derived sample obtained through such steps is measured. The present inventors elucidated that the cofactor activity of a bispecific antibody that binds to coagulation factor IX or activated coagulation factor IX and to coagulation factor X can be evaluated using the amount of thrombin generated in a blood-derived sample as an indicator. That is, the present invention provides a method for evaluating blood coagulation reaction mediated by a substance having the activity of substituting for coagulation factor VIII (preferably a bispecific antibody that binds to coagulation factor IX or activated coagulation factor IX and to coagulation factor X), using the amount of thrombin generated in a blood-derived sample as an indicator. The amount of thrombin generated in a blood-derived sample can be measured by methods well-known to those skilled in the art. For example, it can be measured by adding a reagent to convert the amount of thrombin in a sample and calculating the maximum amount of thrombin (peak height) and the total amount of thrombin (ETP) by a commercially available apparatus, without limitation thereto.

In the present invention, the cofactor activity of a bispecific antibody that binds to coagulation factor IX or activated coagulation factor IX and to coagulation factor X can be evaluated with appropriate sensitivity using the amount of thrombin generated in a blood-derived sample as an indicator. Cofactor activity necessary for hemostatic action can be evaluated based on, for example, correlation between the clinical effect of a substance having an activity of substituting for coagulation factor VIII and the amount of thrombin generation in a method of the present invention, or comparison between the amount of thrombin generated in a blood-derived sample containing a substance having an activity of substituting for factor VIII and the amount of thrombin generated in a blood-derived sample containing coagulation factor VIII activity, in a method of the present invention. For example, in the present invention, if the concentrations of activated coagulation factor XI and phospholipids in the blood coagulation initiation reagent are adjusted so that the lowest detectable level of thrombin generation reaction can be seen in a blood-derived sample having a coagulation factor VIII activity (FVIII:C) of 1% or in a blood-derived sample supplemented with coagulation factor VIII to attain an FVIII:C of 1%, a substance having coagulation factor VIII-substituting activity administered to a subject can be evaluated as having an activity of inducing blood coagulation reaction, that is, having a hemostatic effect, by the presence of thrombin generation reaction. Alternatively in the present invention, for example, when the amount of thrombin generated in a blood-derived sample isolated from a subject (severe hemophilia A patient) who has received a substance having coagulation factor VIII-substituting activity is about the same as or more than the amount of thrombin generated in a sample prepared by adding 0.01 U/mL of coagulation factor VIII to a blood-derived sample from the same subject that does not contain the substance having coagulation factor VIII-substituting activity or is in such a state that the action of the substance is not shown (comparative sample), the substance having coagulation factor VIII-substituting activity administered to the subject can be evaluated as having an activity of inducing blood coagulation reaction, that is, having a hemostatic effect. The expression, "the amount of thrombin generated is about the same" may mean that the amount of thrombin generated in a blood-derived sample from a subject who has received a substance having coagulation factor VIII-substituting activity is, for example, plus or minus 100% or less, preferably 50% or less, particularly preferably 20% or less of the amount of thrombin generated in a comparative sample, but is not limited thereto. The amount of thrombin generated can be determined using, for example, the maximum amount of thrombin (peak height) and total amount of thrombin (ETP) as indicators.

Furthermore, the present invention provides blood coagulation initiation reagents to be used for evaluation of blood coagulation reaction of the present invention. The blood coagulation initiation reagents of the present invention contain activated coagulation factor XI. The blood coagulation initiation reagents of the present invention can further contain phospholipids. Examples of the phospholipids are described above. The blood coagulation initiation reagents of the present invention can additionally include salts of calcium, magnesium, and such.

The "blood coagulation initiation reagent to be used for evaluation of blood coagulation reaction of the present invention" can be rephrased as "use of activated coagulation factor XI, or activated coagulation factor XI and phospholipids, in the production of a blood coagulation initiation reagent to be used for evaluating blood coagulation reaction". Furthermore, it may be rephrased as "activated coagulation factor XI, or activated coagulation factor XI and phospholipids for use in evaluating blood coagulation reaction". Furthermore, the blood coagulation initiation reagent of the present invention can be expressed as "a method for producing a blood coagulation initiation reagent for evaluating blood coagulation reaction, which comprises the step of formulating activated coagulation factor XI, or activated coagulation factor XI and phospholipids, with a pharmaceutically or physiologically acceptable carrier". Herein, activated coagulation factor XI includes coagulation factor XI as long as it is added externally to a blood-derived sample. Activated coagulation factor XI of the present invention may be any of those commercially available, purified from plasma, or produced by genetic recombination techniques. Methods for obtaining them are well-known to those skilled in the art.

Various reagents such as blood coagulation initiation reagents necessary for a method for evaluating blood coagulation reaction of the present invention can be packaged in advance and provided as a kit. A kit of the present invention may include, in addition to a blood coagulation initiation reagent, a positive control of plasma sample isolated from a human whose coagulation factor VIII activity and coagulation factor IX activity in the blood are normal, a substance having an activity of substituting for coagulation factor VIII, and materials that can be used in a thrombin generation assay (for example, a fluorogenic substrate for thrombin, a reagent for converting the amount of thrombin in a sample, and such). Furthermore, the various reagents included in the kit can be in a powder or liquid form according to the mode of their use. Furthermore, they can be stored in appropriate containers and used when suitable.

All prior art references cited herein are incorporated by reference into this description.

EXAMPLES

Herein below, the present invention will be specifically described with reference to the Examples, but it is not to be construed as being limited thereto.

Preparation of Anti-FIXa/FX Bispecific Antibodies Having FVIII Function-Substituting Activity, and Measurement of the FVIII Function-Substituting Activity Anti-FIXa/FX-bispecific antibodies having FVIII-function-substituting activity were obtained by the methods described in WO2005/035756, WO2006/109592, and WO2012/067176. The antibody genes described in WO2005/035756, WO2006/109592, and WO2012/067176 were incorporated into an animal cell expression vector, and they were transfected into HEK293 cells to transiently express the bispecific antibodies. Then, bispecific antibodies contained in the cell culture supernatant were purified using Protein A and gel filtration.

Measurement of the FVIII function-substituting activity of the thus purified bispecific antibodies was carried out by the following enzyme assay. Under room temperature, 1 nM human FIXa (Enzyme Research Laboratories), 140 nM human FX (Enzyme Research Laboratories), 20 μM phospholipids (10% phosphatidylserine, 60% phosphatidylcholine, and 30% phosphatidylethanolamine), and a bispecific antibody were mixed in an aqueous Tris buffered physiological saline solution containing 5 mM $CaCl_2$ and 0.1% bovine serum albumin, and incubated for two minutes to allow the FX activation reaction by FIXa to proceed. This reaction was terminated by addition of EDTA. Next, FXa-specific chromogenic substrate solution S-2222® (CHROMOGENIX) was added, and absorbance changes at 405 nm were measured using SPECTRAMAX® 340PC$^{384}$ (Molecular Devices). A calibration curve was produced from absorbance changes using known concentrations of human FXa (Enzyme Research Laboratories), and the bispecific antibodies were evaluated for the FXa generation-promoting activity.

APTT Measurement

Measurement was performed by using Thrombocheck APTT-SLA (Sysmex) as an APTT reagent, and by following a standard APTT measurement protocol. To 50 μL of factor VIII (FVIII)-deficient human plasma (commercial product from George King Bio-Medical) or FVIII-deficient plasma with inhibitor (commercial product from George King Bio-Medical) containing a bispecific antibody or recombinant human FVIII (rhFVIII, Bayer), 50 μL of the APTT reagent was added. After incubation for three minutes, 50 μL of 0.02 mol/L calcium chloride solution was added to initiate coagulation reaction, and APTT was measured using an automated blood coagulation analyzer (KC4 Delta, Trinity Biotech).

Thrombin Generation Assay

A thrombogram was obtained by calibrated automated thrombography using a 96-well plate fluorometer (Thermo Fisher Scientific Instruments) equipped with a 390-nm excitation wavelength/460-nm fluorescence wavelength filter set, dispenser, and analysis software (THROMIBINOSCOPE® software version 3.0.0.29, Thrombinoscope BV). To each well, 80 μL of the factor VIII (FVIII)-deficient human plasma or FVIII-deficient plasma with inhibitor (George King Bio-Medical) containing a bispecific antibody or recombinant human FVIII (rhFVIII, Bayer) was added. Next, 20 μL of a coagulation initiation reagent (FXIa/phospholipid reagent) containing 0.47 nM human factor XIa (Enzyme Research Laboratories) and 20 μM phospholipids, or PPP-Reagent LOW (Thrombinoscope BV) was added. For conversion to thrombin amount, 20 μL of Thrombin Calibrator (Thrombinoscope BV) was added instead of the coagulation initiation reagent. To initiate the reaction, 20 μL of FluCa reagent prepared from FluCa kit (Thrombinoscope BV) was automatically dispensed from a programmed apparatus. The thrombogram, peak height (maximum amount of thrombin), and ETP (total amount of thrombin) were calculated using the software of the apparatus.

Hemophilia A Model

Hybridomas were produced from mice immunized with human FVIII, and then an anti-FVIII neutralizing antibody that cross-reacts with cynomolgus monkey but not with pig was identified. Cross-reactivity with cynomolgus monkey and pig was confirmed by adding the antibody to citrated plasma of each animal, and determining whether coagulation is inhibited by APTT or thrombin generation assay. This anti-FVIII antibody was administered to cynomolgus monkeys at a dose that can extend the APTT by two-fold, to produce an acquired hemophilia A condition. Next, as a test drug, 0.3 mg/kg of hBS23 (n=3), which is one of the bispecific antibodies, or 1 U/kg of pig FVIII (n=3) was administered intravenously to the animals. Pig FVIII was prepared and purified by conventional methods using genetic recombination techniques. A group without administration of the drug (n=6) was also set up as a control. Bleeding was induced artificially in animals under anesthesia (the muscles of the forearm, upper arm, and thigh are punctured with an 18G needle), and then the animals were observed up to three days later. In the group to which 1 U/kg of pig FVIII was administered, 1 U/kg of pig FVIII was additionally administered intravenously to the animal twice a day (six times in total; no administration on the last day of observation). This is a regimen designed to maintain the plasma FVIII activity at 0.01 U/mL or more. As indicators for bleeding, hemoglobin values (reflecting anemia due to blood loss) and purple-colored area of the skin (bleeding marks) were employed.

Results

<FVIII Function-Substituting Activity of Bispecific Antibody>

One of the bispecific antibodies, hBS23, showed FXa generation-promoting activity in the presence of FIXa/FX/phospholipids, demonstrating that it has FVIII function-substituting activity (FIG. 1).

<In Vivo Hemostasis Activity of Bispecific Antibody>

In the control animals, progressive decrease in the hemoglobin value and enlargement of the purple-colored area of the skin were observed up to three days later. These were suppressed by a single intravenous administration of hBS23 or by repeated intravenous administration (twice a day) of 1 U/kg of pig FVIII. The degree of suppression was about the same in both cases.

The plasma concentration of hBS23 during the experiment period was about 30 nM (40 to 18 nM on average in a group), suggesting that hBS23 at around this concentration has hemostasis activity that is approximately equal to that of the regimen for maintaining the plasma FVIII activity at 0.01 U/mL (1% FVIII activity) or more (repeated intravenous administration (twice a day) of 1 U/kg of pig FVIII).

<Activity of Bispecific Antibody in Plasma Assay>

Figure 2:
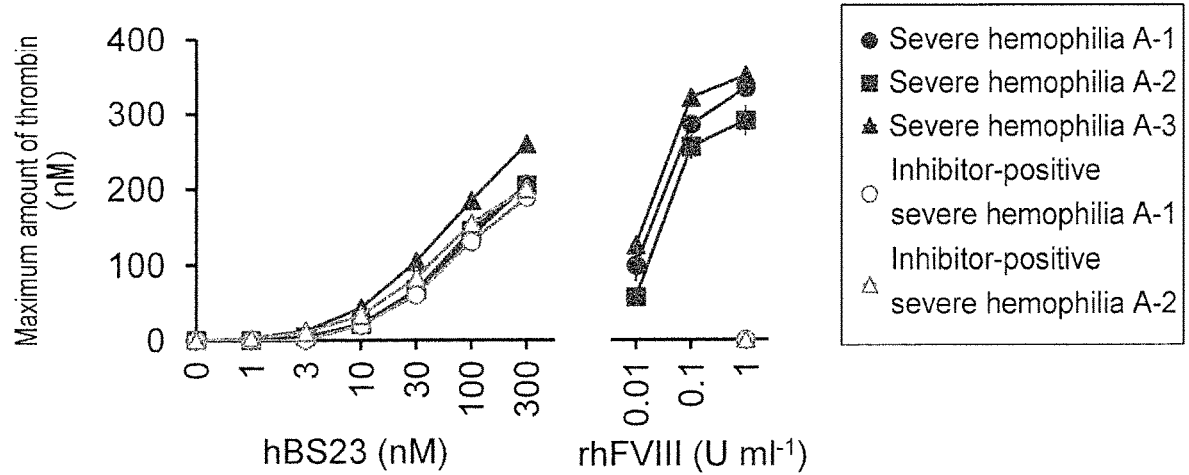
FIG. 2 shows the effects of hBS23 and recombinant human coagulation factor VIII (rhFVIII) on thrombin generation assay parameters (Peak height (A) and endogenous thrombin potential (ETP) (B)) of FVIII-deficient plasma or FVIII-deficient plasma with inhibitor. Each lot of plasma was obtained from a single donor confirmed to have severe hemophilia A (Plasma 1, 2, 3) or inhibitor-positive severe hemophilia A (Plasma with inhibitor 1, 2). Inhibitor titers were 292 and 148 Bethesda units for Plasma with inhibitor 1 and 2, respectively. In FVIII-deficient plasma and in FVIII-deficient plasma with inhibitor, hBS23 increased the Peak height and ETP in a concentration-dependent manner under FXIa/phospholipid reagent-induced conditions.
Figure 2:
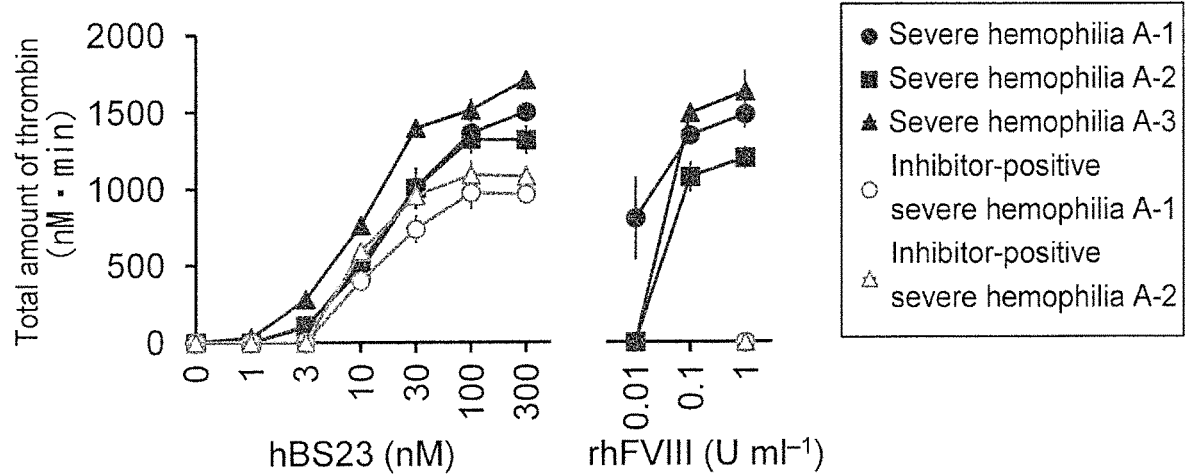

One of the bispecific antibodies, hBS23, increased the peak height (maximum amount of thrombin) and ETP (total amount of thrombin), which are parameters for thrombin generation, in a concentration-dependent manner under FXIa/phospholipid reagent-induced conditions in FVIII-deficient plasma (FIG. 2). According to peak height analysis, 30 nM of hBS23 has activity corresponding to 0.01 U/mL of rhFVIII (1% FVIII activity), and 300 nM hBS23 has activity close to 0.1 U/mL of rhFVIII (10% FVIII activity). As described above, in the in vivo assay, hemostasis activity equivalent to that of the regimen for maintaining the plasma FVIII activity at 0.01 U/mL (1% FVIII activity) or more was obtained by keeping the concentration of hBS23 at about 30 nM. Therefore, it was suggested that thrombin generation assay would be a monitoring method reflecting the hemostatic action of hBS23 with appropriate sensitivity.

On the other hand, when thrombin generation assay was performed under PPP-Reagent LOW (coagulation initiation reagent containing a low concentration of tissue factor)-induced conditions, the measurement sensitivity of hBS23 activity and rhFVIII was low as compared to that under the FXIa/phospholipid reagent-induced conditions, and therefore appropriate reflection of in vivo hemostatic action was considered to be difficult. Furthermore, when the APTT value was used to evaluate the FVIII-specific activity of hBS23, the specific activity of hBS23 at 30 nM or more was calculated as 1 U/mL (100% FVIII activity) or more of FVIII. This result suggested that FVIII activity of hBS23 calculated from the APTT value may be greater than the hemostatic action in the in vivo assay.

INDUSTRIAL APPLICABILITY

The present invention provides a method for evaluating the effect of a bispecific antibody having an activity of functionally substituting for FVIII on blood coagulation reaction. By using the methods of the present invention, it is possible to determine with appropriate sensitivity the effect of such a bispecific antibody in the treatment of a hemorrhagic disease such as hemophilia.

---

The invention claimed is:

1. A method for evaluating blood coagulation reaction mediated by a substance having an activity of substituting for coagulation factor VIII, wherein the method comprises:
   (i) adding a blood coagulation initiation reagent comprising activated coagulation factor XI and a phospholipid to a blood-derived sample isolated from a subject, wherein the coagulation initiation reagent does not comprise tissue factor, and wherein the sample comprises the substance having an activity of substituting for coagulation factor VIII; and
   (ii) measuring the amount of thrombin generated in the blood-derived sample obtained in (i),
   wherein the subject is a hemorrhagic disease patient,
   wherein the substance having the activity of substituting for coagulation factor VIII has been administered to the subject, and
   wherein the substance having the activity of substituting for coagulation factor VIII is a bispecific antibody that binds to coagulation factor IX or activated coagulation factor IX, and to coagulation factor X.

2. The method of claim 1 wherein the hemorrhagic disease is a disease caused by decreased or deficient activity of coagulation factor VIII or activated coagulation factor VIII.

3. The method of claim 1, wherein the hemorrhagic disease is a disease selected from the group consisting of hemophilia, acquired hemophilia, and von Willebrand's disease caused by dysfunction or deficiency of von Willebrand factor (vWF).

4. The method of claim 1, wherein the phospholipid comprises a member selected from the group consisting of phosphatidylserine, phosphatidylcholine, phosphatidylethanolamine, phosphatidylinositol, phosphatidylglycerol, diphosphatidylglycerol, and sphyngomyelin.

5. The method of claim 4, wherein the phospholipid comprises a combination of phosphatidylserine, phosphatidylcholine, and phosphatidylethanolamine.

6. The method of claim 1, wherein the blood coagulation initiation reagent comprises the activated coagulation factor XI and phospholipid at concentrations sufficient to detect thrombin generation in a control blood-derived sample having a coagulation factor VIII activity of 1%.

7. The method of claim 1, wherein the measuring the amount of thrombin generated comprises determining the total amount of thrombin generated.

8. The method of claim 1, wherein measuring the amount of thrombin generated comprises determining the maximum rate of thrombin generation.

* * * * *

SEQUENCE LISTING

```
<160> NUMBER OF SEQ ID NOS: 2

<210> SEQ ID NO 1
<211> LENGTH: 625
<212> TYPE: PRT
<213> ORGANISM: Homo sapiens

<400> SEQUENCE: 1

Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30

Gly Asp Ile Thr Thr Val Phe Thr Pro Ser Ala Lys Tyr Cys Gln Val
        35                  40                  45

Val Cys Thr Tyr His Pro Arg Cys Leu Leu Phe Thr Phe Thr Ala Glu
    50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
                85                  90                  95

Gly Tyr Ser Phe Lys Gln Cys Ser His Gln Ile Ser Ala Cys Asn Lys
            100                 105                 110

Asp Ile Tyr Val Asp Leu Asp Met Lys Gly Ile Asn Tyr Asn Ser Ser
        115                 120                 125

Val Ala Lys Ser Ala Gln Glu Cys Gln Glu Arg Cys Thr Asp Asp Val
    130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
                165                 170                 175
```

-continued

```
Arg Ile Thr Lys Leu Asp Lys Val Val Ser Gly Phe Ser Leu Lys Ser
            180                 185                 190
Cys Ala Leu Ser Asn Leu Ala Cys Ile Arg Asp Ile Phe Pro Asn Thr
            195                 200                 205
Val Phe Ala Asp Ser Asn Ile Asp Ser Val Met Ala Pro Asp Ala Phe
210                 215                 220
Val Cys Gly Arg Ile Cys Thr His His Pro Gly Cys Leu Phe Phe Thr
225                 230                 235                 240
Phe Phe Ser Gln Glu Trp Pro Lys Glu Ser Gln Arg Asn Leu Cys Leu
            245                 250                 255
Leu Lys Thr Ser Glu Ser Gly Leu Pro Ser Thr Arg Ile Lys Lys Ser
            260                 265                 270
Lys Ala Leu Ser Gly Phe Ser Leu Gln Ser Cys Arg His Ser Ile Pro
            275                 280                 285
Val Phe Cys His Ser Ser Phe Tyr His Asp Thr Asp Phe Leu Gly Glu
290                 295                 300
Glu Leu Asp Ile Val Ala Ala Lys Ser His Glu Ala Cys Gln Lys Leu
305                 310                 315                 320
Cys Thr Asn Ala Val Arg Cys Gln Phe Phe Thr Tyr Thr Pro Ala Gln
            325                 330                 335
Ala Ser Cys Asn Glu Gly Lys Gly Lys Cys Tyr Leu Lys Leu Ser Ser
            340                 345                 350
Asn Gly Ser Pro Thr Lys Ile Leu His Gly Arg Gly Ile Ser Gly
            355                 360                 365
Tyr Thr Leu Arg Leu Cys Lys Met Asp Asn Glu Cys Thr Thr Lys Ile
370                 375                 380
Lys Pro Arg Ile Val Gly Gly Thr Ala Ser Val Arg Gly Glu Trp Pro
385                 390                 395                 400
Trp Gln Val Thr Leu His Thr Thr Ser Pro Thr Gln Arg His Leu Cys
            405                 410                 415
Gly Gly Ser Ile Ile Gly Asn Gln Trp Ile Leu Thr Ala Ala His Cys
            420                 425                 430
Phe Tyr Gly Val Glu Ser Pro Lys Ile Leu Arg Val Tyr Ser Gly Ile
            435                 440                 445
Leu Asn Gln Ser Glu Ile Lys Glu Asp Thr Ser Phe Phe Gly Val Gln
450                 455                 460
Glu Ile Ile Ile His Asp Gln Tyr Lys Met Ala Glu Ser Gly Tyr Asp
465                 470                 475                 480
Ile Ala Leu Leu Lys Leu Glu Thr Thr Val Asn Tyr Thr Asp Ser Gln
            485                 490                 495
Arg Pro Ile Cys Leu Pro Ser Lys Gly Asp Arg Asn Val Ile Tyr Thr
            500                 505                 510
Asp Cys Trp Val Thr Gly Trp Gly Tyr Arg Lys Leu Arg Asp Lys Ile
            515                 520                 525
Gln Asn Thr Leu Gln Lys Ala Lys Ile Pro Leu Val Thr Asn Glu Glu
            530                 535                 540
Cys Gln Lys Arg Tyr Arg Gly His Lys Ile Thr His Lys Met Ile Cys
545                 550                 555                 560
Ala Gly Tyr Arg Glu Gly Gly Lys Asp Ala Cys Lys Gly Asp Ser Gly
            565                 570                 575
Gly Pro Leu Ser Cys Lys His Asn Glu Val Trp His Leu Val Gly Ile
            580                 585                 590
Thr Ser Trp Gly Glu Gly Cys Ala Gln Arg Glu Arg Pro Gly Val Tyr
```

```
              595                 600                 605
Thr Asn Val Val Glu Tyr Val Asp Trp Ile Leu Glu Lys Thr Gln Ala
    610                 615                 620
Val
625

<210> SEQ ID NO 2
<211> LENGTH: 3278
<212> TYPE: DNA
<213> ORGANISM: Homo sapiens

<400> SEQUENCE: 2
aggcacacag gcaaaatcaa gttctacatc tgtccctgtg tatgtcactt gtttgaatac      60
gaaataaaat taaaaaaata aattcagtgt attgagaaag caagcaattc tctcaaggta     120
tatttctgac atactaagat tttaacgact ttcacaaata tgctgtactg agagagaatg     180
ttacataaca ttgagaacta gtacaagtaa atattaaagt gaagtgacca tttcctacac     240
aagctcattc agaggaggat gaagaccatt ttggaggaag aaaagcaccc ttattaagaa     300
ttgcagcaag taagccaaca aggtcttttc aggatgattt tcttatatca agtggtacat     360
ttcattttat ttacttcagt ttctggtgaa tgtgtgactc agttgttgaa ggacacctgc     420
tttgaaggag gggacattac tacggtcttc acaccaagcg ccaagtactg ccaggtagtc     480
tgcacttacc acccaagatg tttactcttc actttcacgg cggaatcacc atctgaggat     540
cccacccgat ggtttacttg tgtcctgaaa gacagtgtta cagaaacact gccaagagtg     600
aataggacag cagcgatttc tgggtattct ttcaagcaat gctcacacca ataagcgct     660 tgcaacaaag acatttatgt ggacctagac atgaagggca taaactataa cagctcagtt     720
gccaagagtg ctcaagaatg ccaagaaaga tgcacggatg acgtccactg ccacttttc     780 acgtacgcca caaggcagtt tcccagcctg agcatcgta acatttgtct actgaagcac     840
acccaaacag gcaccaac cagaataacg aagctcgata agtggtgtc tggattttca     900 ctgaaatcct gtgcactttc taatctggct tgtattaggg cattttccc taatacggtg     960 tttgcagaca gcaacatcga cagtgtcatg gctcccgatg cttttgtctg tggccgaatc    1020
tgcactcatc atcccggttg cttgtttttt accttctttt cccaggaatg gcccaaagaa    1080
tctcaaagaa atctttgtct ccttaaaaca tctgagagtg gattgcccag tacacgcatt    1140
aaaaagagca aagctctttc tggtttcagt ctacaaagct gcaggcacag catcccagtg    1200
ttctgccatt cttcattta ccatgacact gatttcttgg gagaagaact ggatattgtt    1260
gctgcaaaaa gtcacgaggc ctgccagaaa ctgtgcacca atgccgtccg ctgccagttt    1320
tttacctata ccccagccca agcatcctgc aacgaaggga agggcaagtg ttacttaaag    1380
ctttcttcaa acggatctcc aactaaaata cttcacggga gaggaggcat ctctggatac    1440
acattaaggt tgtgtaaaat ggataatgag tgtaccacca aaatcaagcc aggatcgtt    1500 ggaggaactg cgtctgttcg tggtgagtgg ccgtggcagg tgaccctgca cacaacctca    1560
cccactcaga gacacctgtg tggaggctcc atcattggaa accagtggat attaacagcc    1620
gctcactgtt tctatggggt agagtcacct aagattttgc gtgtctacag tggcatttta    1680
aatcaatctg aaataaaaga ggacacatct ttctttgggg ttcaagaaat aataatccat    1740
gatcagtata aaatggcaga aagcgggtat gatattgcct tgttgaaact ggaaaccaca    1800
gtgaattaca cagattctca acgacccata tgcctgcctt ccaaaggaga tagaaatgta    1860
atatacactg attgctgggt gactggatgg gggtacagaa aactaagaga caaaatacaa    1920
```

```
aatactctcc agaaagccaa gatacccttta gtgaccaacg aagagtgcca gaagagatac    1980
agaggacata aaataaccca taagatgatc tgtgccggct acagggaagg agggaaggac    2040
gcttgcaagg gagattcggg aggccctctg tcctgcaaac acaatgaggt ctggcatctg    2100
gtaggcatca cgagctgggg cgaaggctgt gctcaaaggg agcggccagg tgtttacacc    2160
aacgtggtcg agtacgtgga ctggattctg gagaaaactc aagcagtgtg aatgggttcc    2220
caggggccat tggagtccct gaaggaccca ggatttgctg ggagagggtg ttgagttcac    2280
tgtgccagca tgcttcctcc acagtaacac gctgaagggg cttggtgttt gtaagaaaat    2340
gctagaagaa aacaaactgt cacaagttgt tatgtccaaa actcccgttc tatgatcgtt    2400
gtagtttgtt tgagcattca gtctctttgt ttttgatcac gcttctatgg agtccaagaa    2460
ttaccataag gcaatatttc tgaagattac tatataggca gatatagcag aaaataacca    2520
agtagtggca gtggggatca ggcagaagaa ctggtaaaag aagccaccat aaatagattt    2580
gttcgatgaa agatgaaaac tggaagaaag gagaacaaag acagtcttca ccattttgca    2640
ggaatctaca ctctgcctat gtgaacacat ttcttttgta aagaaagaaa ttgattgcat    2700
ttaatggcag atttttcagaa tagtcaggaa ttcttgtcat ttccattta aaatatatat     2760 taaaaaaat cagttcgagt agacacgagc taagagtgaa tgtgaagata acagaatttc    2820
tgtgtggaag aggattacaa gcagcaattt acctggaagt gataccttag gggcaatctt    2880
gaagatacac tttcctgaaa aatgatttgt gatggattgt atatttattt aaaatatctt    2940
gggaggggag gctgatggag ataggggagca tgctcaaacc tccctaagac aagctgctgc    3000
tgtgactatg ggctcccaaa gagctagatc gtatatttat ttgacaaaaa tcaccataga    3060
ctgcatccat actacagaga aaaaacaatt agggcgcaaa tggatagtta cagtaaagtc    3120
ttcagcaagc agctgcctgt attctaagca ctgggatttt ctgtttcgtg caaatattta    3180
tctcattatt gttgtgatct agttcaataa cctagaattt gaattgtcac cacatagctt    3240
tcaatctgtg ccaacaacta tacaattcat caagtgtg                            3278
```